(12) United States Patent
Steele, Sr.

(10) Patent No.: US 7,648,456 B2
(45) Date of Patent: Jan. 19, 2010

(54) ADAPTER FOR PENILE PROSTHESIS TIP EXTENDER

(75) Inventor: Martin T. Steele, Sr., Otsego, MN (US)

(73) Assignee: Coloplast A/S, Humlebaek (DK)

( * ) Notice: Subject to any disclaimer, the term of this patent is extended or adjusted under 35 U.S.C. 154(b) by 986 days.

(21) Appl. No.: 11/096,478

(22) Filed: Apr. 1, 2005

(65) Prior Publication Data

US 2006/0224039 A1 Oct. 5, 2006

(51) Int. Cl.
*A61F 5/00* (2006.01)
(52) U.S. Cl. .......................................... 600/38
(58) Field of Classification Search ............. 600/38–41; 128/897, 898
See application file for complete search history.

(56) References Cited

U.S. PATENT DOCUMENTS

| | | | | | |
|---|---|---|---|---|---|
| 3,672,708 | A | * | 6/1972 | Zemberry | 285/315 |
| 4,600,223 | A | * | 7/1986 | de Vries | 285/319 |
| 4,943,091 | A | * | 7/1990 | Bartholomew | 285/12 |
| 5,010,882 | A | | 4/1991 | Polyak et al. | |
| 5,782,865 | A | * | 7/1998 | Grotz | 606/232 |
| 6,575,987 | B2 | * | 6/2003 | Gellman et al. | 606/151 |
| 6,808,489 | B2 | | 10/2004 | George et al. | |

FOREIGN PATENT DOCUMENTS

| | | |
|---|---|---|
| EP | 0 428 314 | 1/1997 |
| WO | WO-97/07743 | 3/1997 |

* cited by examiner

*Primary Examiner*—Samuel G Gilbert
(74) *Attorney, Agent, or Firm*—Nicholas Baumann

(57) ABSTRACT

An adapter for holding a rear tip extender onto the cylinder of a penile prosthesis or onto another rear tip extender is described herein.

12 Claims, 9 Drawing Sheets

ADAPTER FOR PENILE PROSTHESIS TIP EXTENDER

TECHNICAL FIELD

This document relates to adapters for holding rear tip extenders onto penile prostheses.

BACKGROUND

Prosthetic penile implants have been used for many years to allow men suffering from impotence to achieve erection. Some penile prostheses have one or more cylinders with chambers that can be inflatable and may be connected to a fluid-filled reservoir via a pump and valve assembly. Typically, the cylinders of such a prosthetic device are implanted into the corpus cavernosae, the reservoir is implanted in the abdomen, and the pump is implanted in the scrotum. During use, the patient can actuate the pump so that fluid is transferred from the reservoir into the cylinders, producing enough rigidity for an erection. To deflate the cylinders and return the penis to a flaccid state, the patient can actuate a valve assembly within the pump so that the fluid in the cylinders is returned to the reservoir. Some penile prostheses include two cylinders that each have an inflatable chamber for disposal within the distal corpus cavernosae and a rear tip for disposal within the proximal corpus cavernosae toward the pubic bone. During use, the chambers are inflated, but the rear tips are not.

Surgery generally is required to implant a penile prosthesis within a patient. To implant a prosthesis, a surgeon typically makes an incision at the base of the penis and dilates each corpus cavernosum to create space for the cylinders. The distal end of the cylinder (the inflatable chamber) is then inserted into the corpus cavernosum, and the proximal end of the cylinder (the rear tip) is inserted into the body toward the pubic bone (e.g., inserted in the crus). To achieve a proper fit, the surgeon may attach one or more rear tip extenders (RTEs) onto the rear tip of the cylinder. An extender may be in the form of cap (e.g., a silicone rubber cap) that fits onto the rear tip to extend the length of the cylinder to a suitable amount. In some cases, more than one RTE is attached to the rear tip. Typically, these RTEs are attached to the rear tip and to each other via friction fits and/or mechanical interference, and separation of the components is inhibited by a vacuum that results when they are pulled in opposite directions.

SUMMARY

The cylinder of a penile implant (e.g., the Mentor TITAN® Inflatable Penile Prosthesis) can have a coating (e.g., a hydrophilic coating) to aid in implantation and, in some cases, to provide antibiotic properties. During implantation, such a coating may become hydrated, resulting in a lubricious surface. As a result of this lubricity, the friction fit engagement of a RTE to the rear tip of the cylinder (or to another RTE) can be reduced, and in some cases, the RTE may separate from the cylinder during or after implantation into a patient.

The adapters provided herein can increase the force required to separate an RTE from the rear tip of a prosthesis cylinder or from another RTE. An adapter can be configured to fit within a RTE and over an outer surface of a rear tip of a prosthesis cylinder. An adapter also can be configured to fit within a RTE and over an outer surface of another RTE. When contained within a RTE, an outer surface of an adapter can be in interference with an inner surface of the RTE. Similarly, when installed on a rear tip, an inner surface of an adapter can be in interference with an outer surface of the rear tip. An adapter can have one or more engagement lips or protrusions, which can be flat or pitched (e.g., threaded). When the adapter is installed on the rear tip of a cylinder, particularly when the rear tip is inserted into a RTE, the engagement lips can exert force against and cause compression of an outer surface of the rear tip. Similarly, when the adapter is installed on a first RTE, particularly when the first RTE is inserted into a second RTE, the engagement lips can exert force against and cause compression of an outer surface of the first RTE. In some cases, the full force performance of an adapter as described herein (e.g., an adapter having pitched engagement lips) can be about 4.9 pounds for a RTE that is 1 cm in length.

In one aspect, the invention features an adapter for holding a rear tip extender onto an outer portion of the rear tip of a penile prosthesis cylinder or another rear tip extender, wherein the adapter fits over the outer portion and within the rear tip extender, wherein the adapter comprises one or more protrusions to exert force against the rear tip when the adapter is installed upon the outer portion, and wherein the one or more protrusions extend at an angle between about 5 degrees and about 140 degrees from the sides of the adapter. The adapter can have two or more fingers, wherein each of the fingers has a protrusion to exert force against the outer portion when the adapter is installed upon the outer portion. The adapter can have side surfaces that are parallel to one another or that are angled with respect to one another. The adapter can have an outer diameter between about 5 mm and about 30 mm or between about 10 mm and about 15 mm. The adapter can have a bottom surface that lies within a plane, wherein each of the one or more protrusions has a top surface, and wherein each of the top surfaces lies within a plane that is parallel to the plane in which the bottom surface lies. Alternatively, the adapter can have a bottom surface that lies within a plane, wherein each of the one or more lips has a top surface, and wherein each of the top surfaces lies within a plane that is not parallel to the plane in which the bottom surface lies. The top surfaces can define a threaded pitch.

In another aspect, the invention features an article of manufacture comprising a rear tip extender for a penile prosthesis cylinder and the adapter described herein, wherein the rear tip extender is in the form of a hollow cone, and wherein the adapter is disposed within the interior of the rear tip extender. The adapter can be adhered to the interior surface of the rear tip extender.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This disclosure relates to penile prostheses that can be coupled to RTEs. In particular, adapters for holding a RTE onto the outer surface of the cylinder of a penile prosthesis or the outer surface of another RTE are provided. These adapters can increase the force with which a RTE is connected to the rear tip of a penile prosthesis or to another RTE, and can reduce the likelihood of separation of the components during or after an implantation procedure. The adapters described herein can be particularly useful when a penile prosthesis has a coating (e.g., a hydrophilic coating) that becomes lubricious during or after implantation into a patient.

Figure 1:
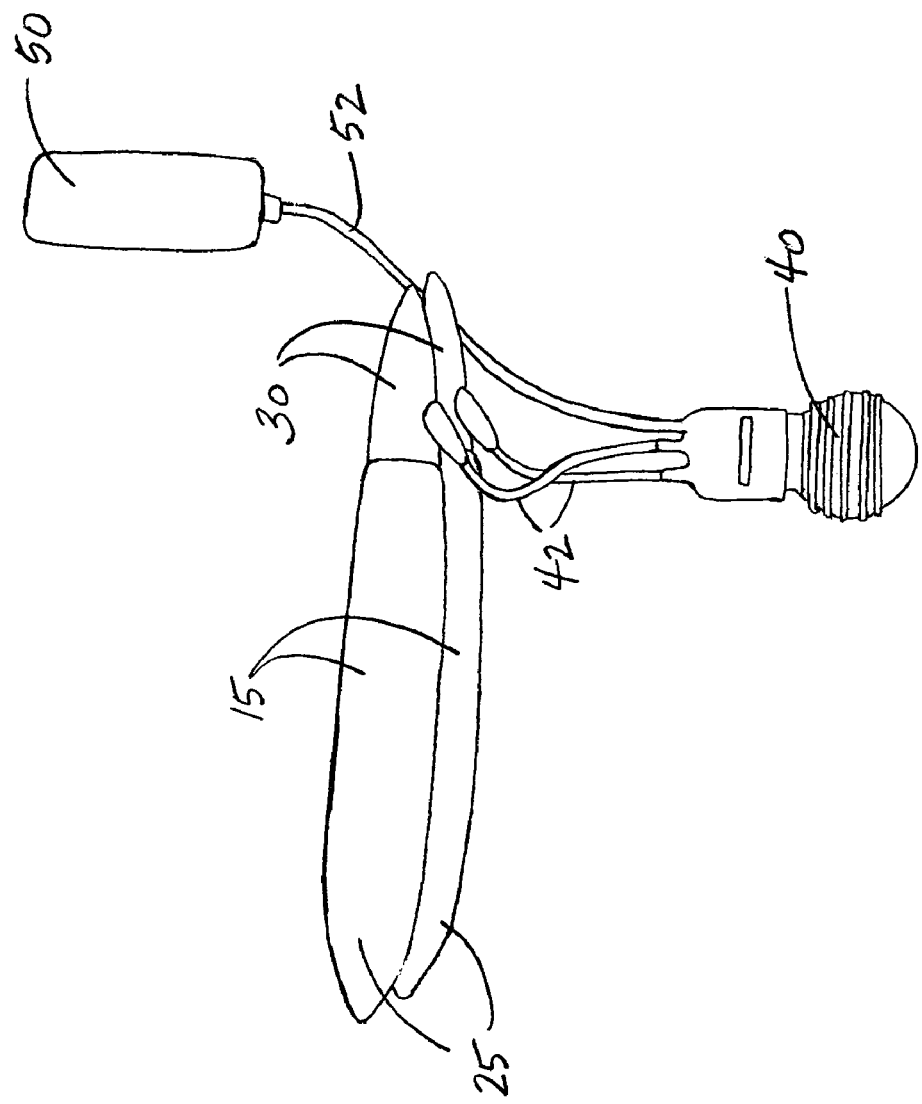
FIG. 1 is a perspective view of a penile prosthesis.

FIG. 1 is a perspective view of penile prosthesis 10. Prosthesis 10 can have a pair of cylinders 15. Each cylinder 15 can have inflatable chamber 25 at its distal end and rear tip 30 at its proximal end. The cylinders can be in fluid communication with pump 40 via tubing 42. Pump 40 can be in fluid communication with reservoir 50 via tubing 52. A user can inflate each chamber 25 by actuating pump 40 such that fluid is transferred from reservoir 50 into the chambers. Fluid can be returned from chambers 25 to reservoir 50 by actuating a valve assembly associated with pump 40. The prosthesis shown in FIG. 1 is a three-piece device. While the adapters described herein are useful with such devices, they also can be used with two-piece devices (e.g., prostheses that lack a reservoir), or with one-piece devices (e.g., prostheses that have neither a reservoir nor a pump and thus are not inflatable).

The distal ends of cylinders 15, each comprising inflation chamber 25, can be implanted within the corpus cavernosae of a patient, while the proximal ends of cylinders 15, each comprising rear tip 30, can be implanted into the patient's pubic region. A RTE can be attached to rear tip 30 such that the length of cylinders 15 is extended toward the area proximate the pubic bone (e.g., toward the crus). A RTE can be an interchangeable piece that fits on rear tip 30. In some cases, more than one RTE can be attached to rear tip 30 to achieve the desired length for cylinder 15, depending on the anatomy of the patient.

Figure 2A:
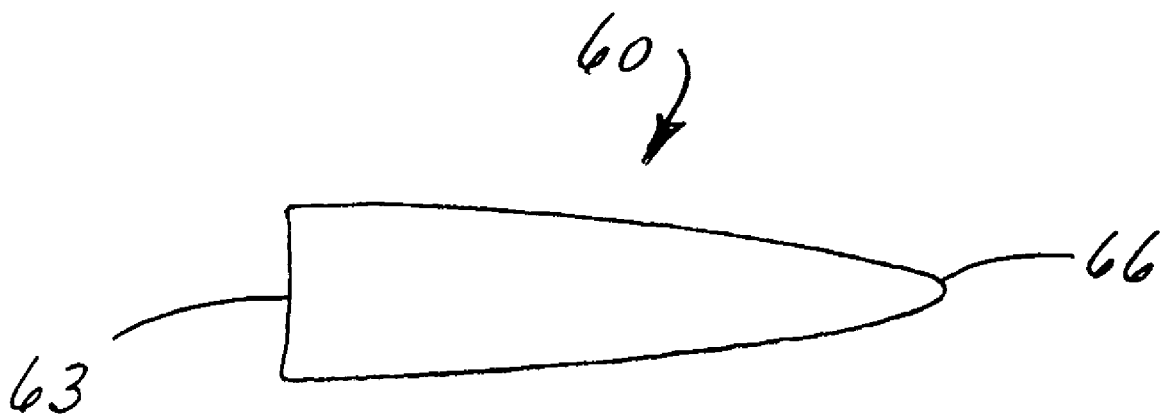
FIG. 2A is a side view of a RTE.
Figure 2B:
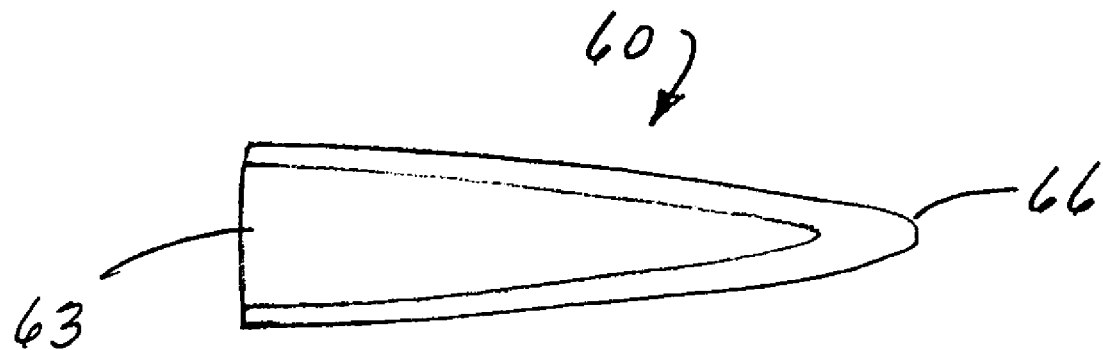
FIG. 2B is a cross-sectional view of a RTE.

FIGS. 2A and 2B show a side view and a cross-sectional view of RTE 60, respectively. RTE 60 can be in the shape of a hollow cone, with open end 63 and tapered closed end 66. RTE 60 can have any dimensions. For example, RTE 60 can have a length between about 0.5 cm and about 5 cm (e.g., about 0.5 cm, about 1 cm, about 1.5 cm, about 2 cm, about 2.5 cm, about 3 cm, about 3.5 cm, about 4 cm, about 4.5 cm, or about 5 cm). RTE 60 also can be made from any suitable material. For example, RTE 60 can be made from a flexible polymer (e.g., a thermoplastic elastomer or a silicone) that can conform around rear tip 30 when rear tip 30 is inserted into open end 63. In the absence of an adapter, RTE 60 can be held onto rear tip 30 by a friction fit or by mechanical interference, for example. When cylinder 15 is coated with a hydrophilic substance, however, such a friction fit may not be sufficient to hold RTE 60 onto rear tip 30 during and after implantation or during removal, if necessary.

As disclosed herein, an adapter can be used to increase the force with which a RTE is connected to the outer surface of the rear tip of a penile prosthesis or to another RTE. An adapter can be made from any suitable material (e.g., a thermoplastic such as polycarbonate, polysulfone, or polyacetal, or a metal). For example, an adapter can be made from a polymer such DELRIN® acetal resin (also known as polyoxymethylene). In some cases, an adapter can be made of the same material used to make a RTE. In addition, an adapter can have any dimensions. An adapter can have a diameter between about 2 mm and about 30 mm (e.g., about 2 mm, about 3 mm about 4 mm, about 5 mm, about 8 mm, about 10 mm, about 12 mm, about 13 mm, about 15 mm, about 17 mm, about 20 mm, about 23 mm, about 25 mm, or about 30 mm). An adapter also can have a length between about 5 mm and about 25 mm (e.g., about 5 mm, about 8 mm, about 10 mm, about 12 mm, about 15 mm, about 17 mm, about 20 mm, about 23 mm, or about 25 mm). Further, an adapter can be made using any suitable method. For example, an adapter can be machined from a suitable polymer, can be made by molding (e.g., by injection molding), or by casting/forming.

Figure 3:
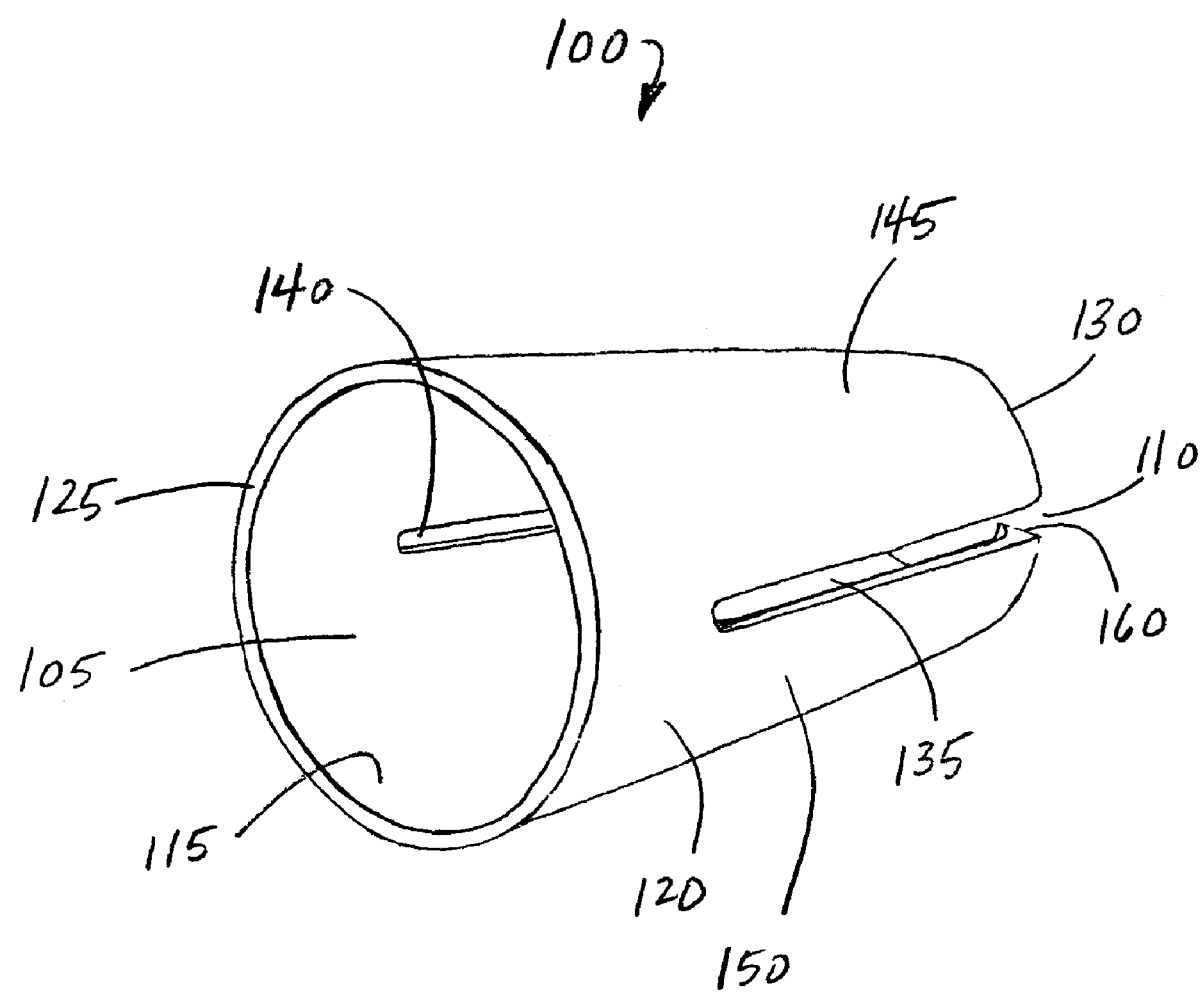
FIG. 3 is a perspective view of an adapter having two fingers.

FIG. 3 is a perspective view of adapter 100. Adapter 100 can be hollow, with first open end 105, second open end 110, inner side surface 115, outer side surface 120, bottom surface 125, and top surface 130. Adapter 100 can have any suitable shape. For example, when bottom surface 125 of adapter 100 is placed against a planar surface, outer side surface 120 can be perpendicular to the planar surface upon which bottom surface 125 rests (i.e., opposing sides of outer side surface 120 can be parallel to one another). In this case, adapter 100 can be in the form of a cylinder, and in some embodiments can have a rectangular cross-section. Alternatively, when bottom surface 125 of adapter 100 is placed against a planar surface, outer side surface 120 can be at an angle of less than 90 degrees with respect to the plane upon which bottom surface 120 rests (i.e., opposing sides of outer side surface 120 can be angled with respect to one another). In this case, adapter 100 can be in the form of a partial cone, and in some embodiments, the cross-section of such an adapter can be trapezoidal.

Inner and outer side surfaces 115 and 120 can be continuous and uninterrupted by slits or other openings. Alternatively, inner and outer side surfaces 115 and 120 can define one or more slits (e.g., slits 135 and 140) that can extend from top surface 130 toward bottom surface 125. The presence of slits such as slits 135 and 140 can divide the sides of adapter 100 into two or more sections or fingers. As shown in FIG. 3, for example, adapter 100 can have fingers 145 and 150. The presence of fingers 145 and 150 can provide adapter 100 with additional flexibility.

Top surface 130 and side surfaces 115 and 120 can define lip 160. When adapter 100 is installed onto the rear tip of a penile prosthesis cylinder, lip 160 can exert force against the rear tip, particularly when the rear tip is inserted into a RTE. Similarly, when adapter 100 is installed onto a RTE, lip 160 can exert force against the RTE, particularly when the RTE is inserted into another RTE. Lip 160 can extend from side surfaces 115 and/or 120 at an angle between about 5 degrees and about 140 degrees (e.g., about 10 degrees, about 20 degrees, about 30 degrees, about 45 degrees, about 50 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, or about 140 degrees). As shown in FIG. 3, for example, lip 160 can extend from outer side surface 120 at an angle between about 70 degrees and about 90 degrees. When slits 135 and 140 are present such that the sides of adapter 100 are divided into fingers 145 and 150, top surface 130 and lip 160 also are divided into two sections.

Figure 4:
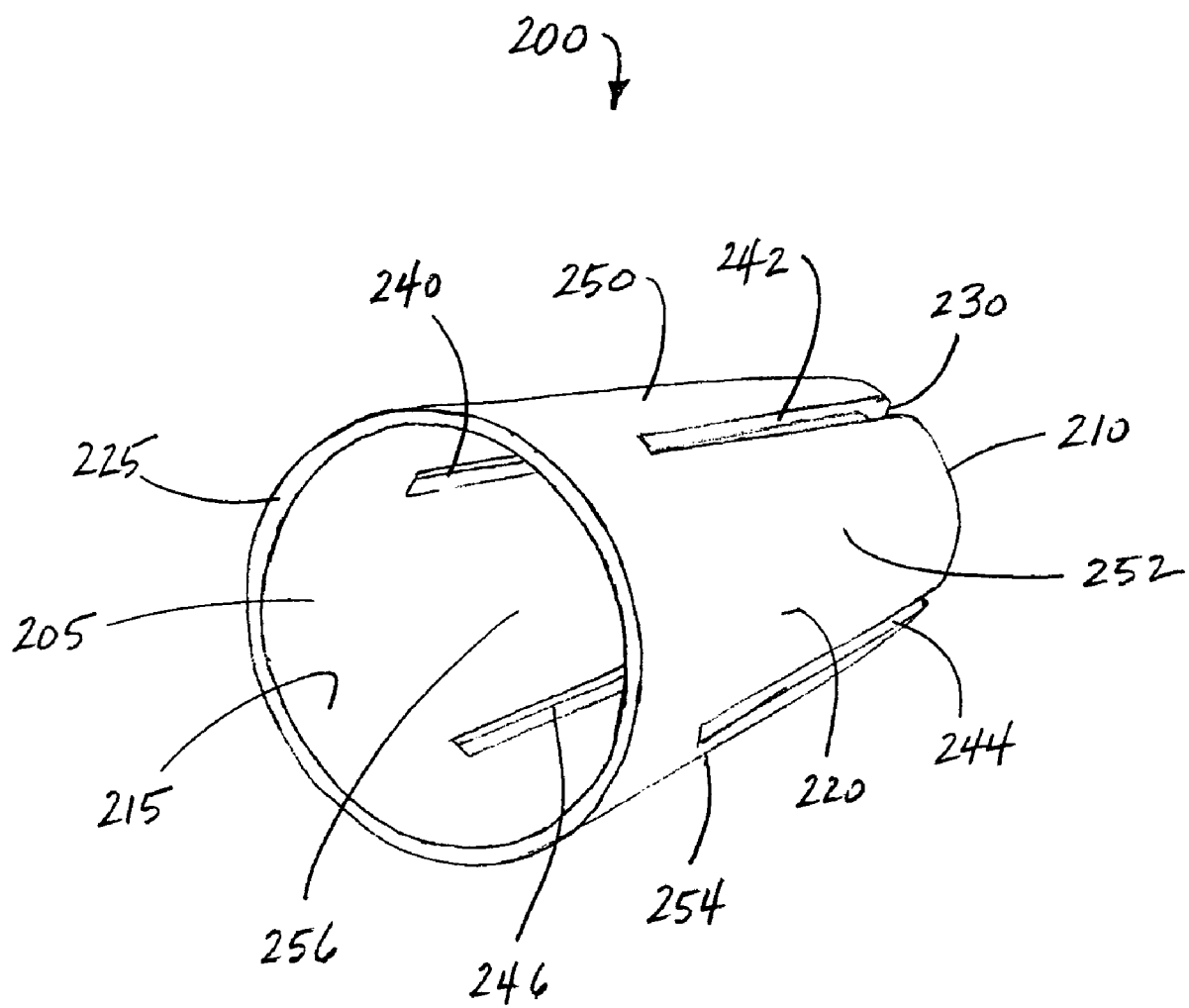
FIG. 4 is a perspective view of an adapter having four fingers.
Figure 5:
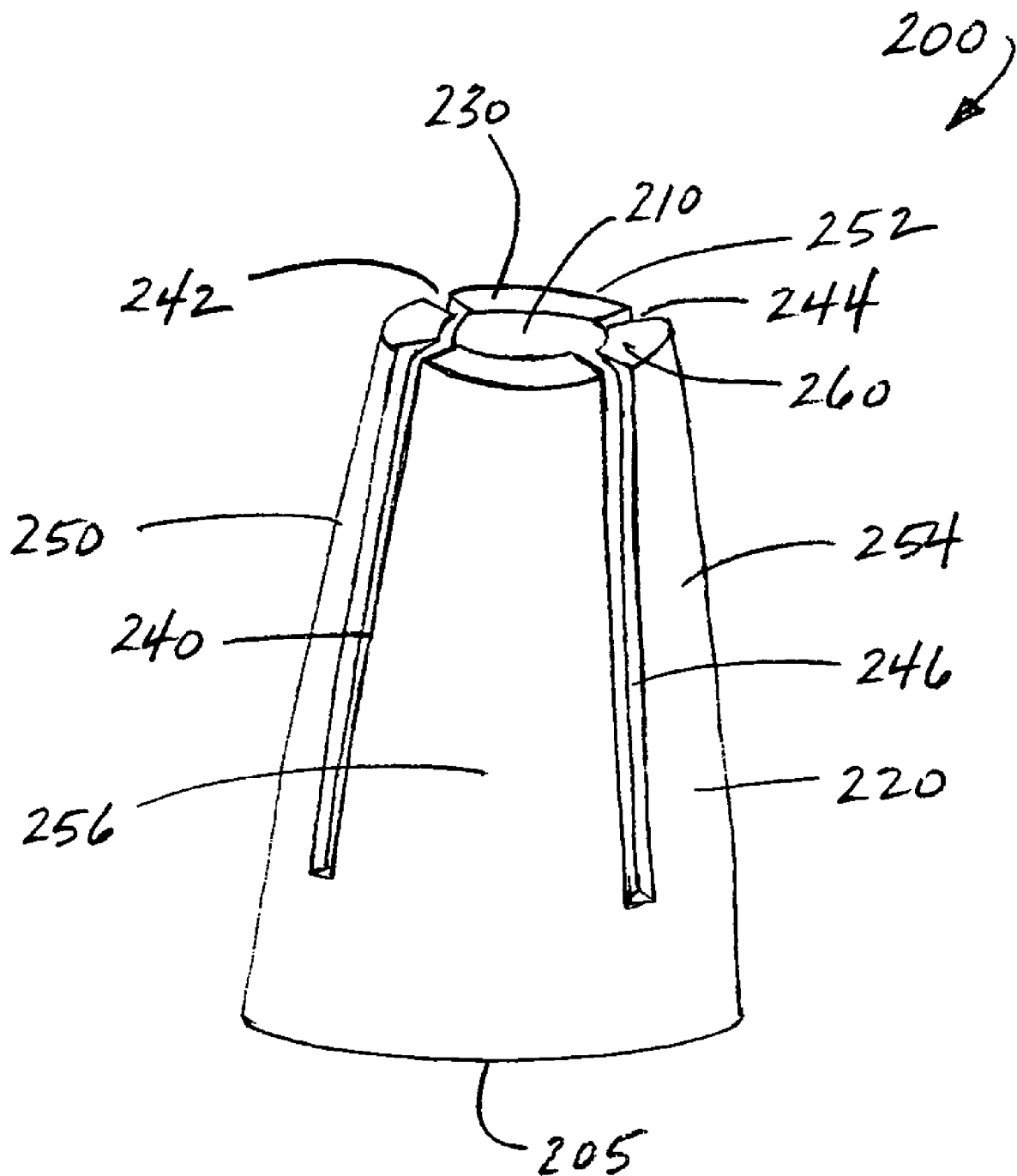
FIG. 5 is a side view of an adapter having four fingers.
Figure 6:
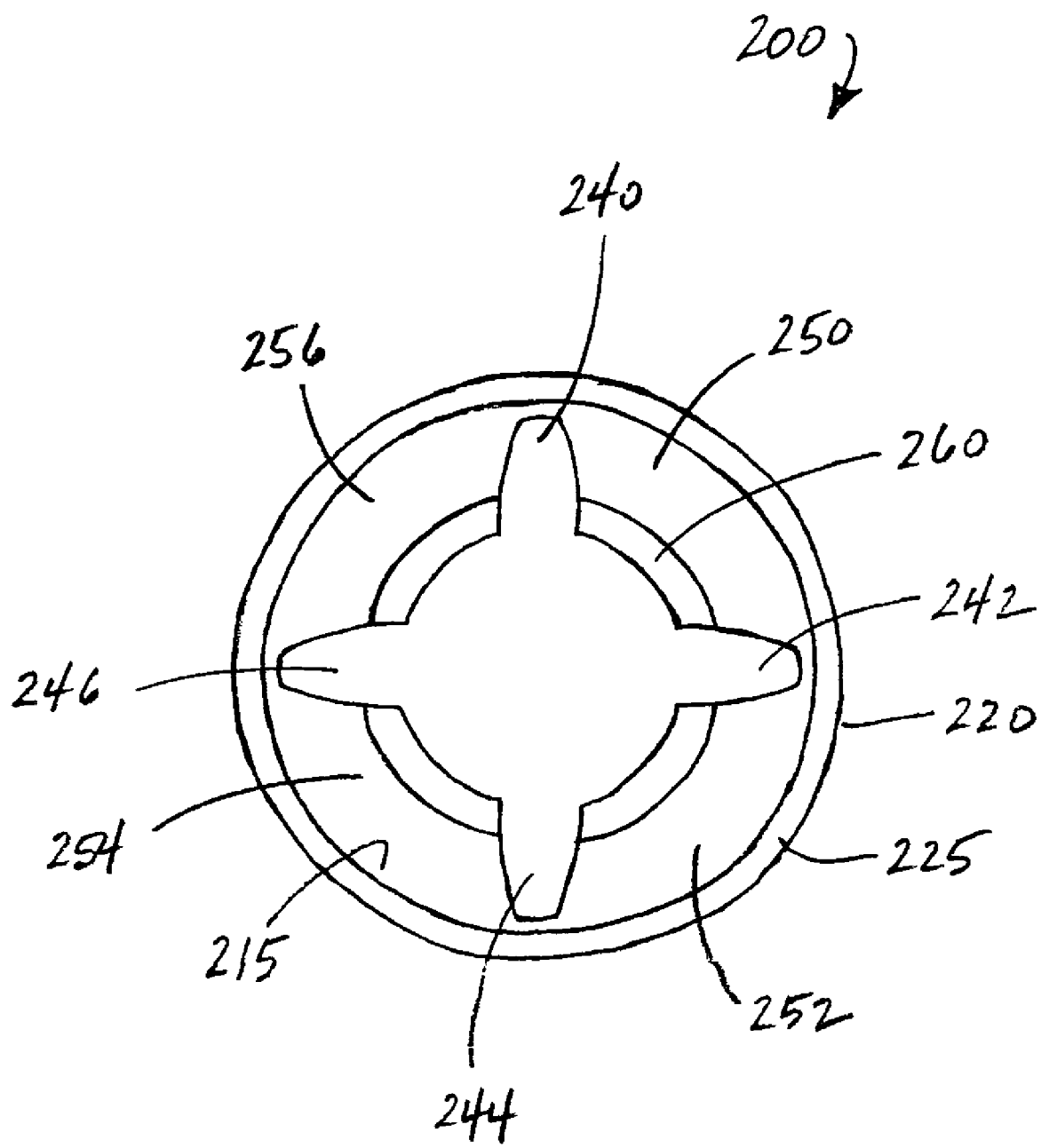
FIG. 6 is an underside view of an adapter having four fingers.
Figure 7:
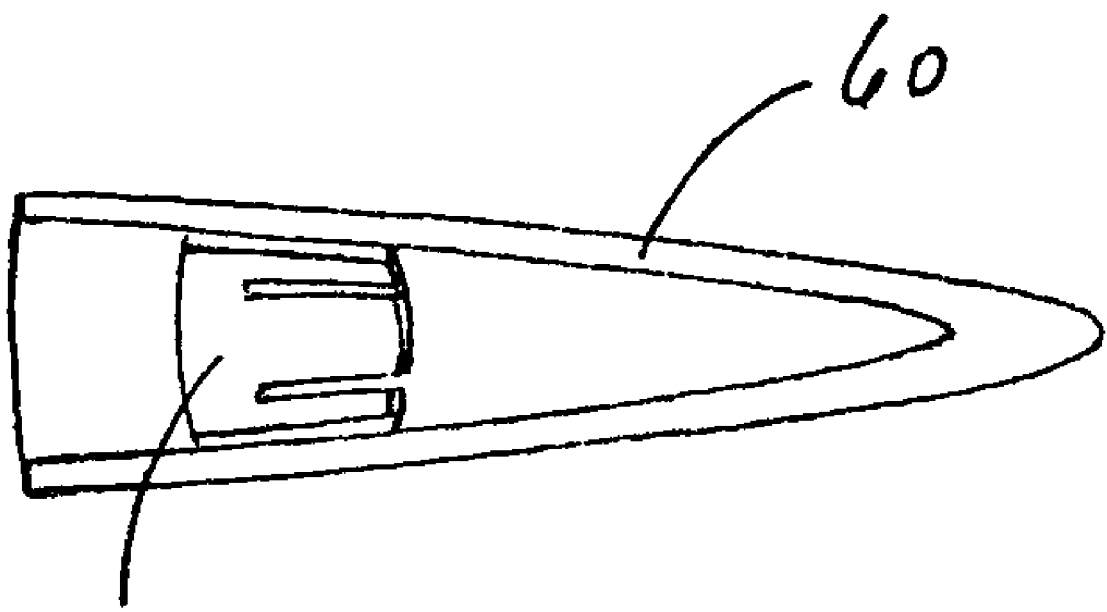
FIG. 7 is a cross-sectional view of a RTE having an adapter disposed therein.

Adapter 200, depicted in FIGS. 4, 5, and 6, can be similar to adapter 100 in that it can be hollow and can have first open end 205, second open end 210, inner side surface 215, outer side surface 220, bottom surface 225, and top surface 230. As shown, adapter 200 can have slits 240, 242, 244, and 246, which can divide sides 215 and 220 into fingers 250, 252, 254, and 256. Adapter 200 also can have lip 260, which, due to the presence of slits 240, 242, 244, and 246 is divided into four sections. Similar to lip 160, lip 260 can extend from the side surfaces of adapter 200 at an angle between about 5 degrees and about 140 degrees. In addition, when adapter 200 is contained within a RTE (e.g., as shown in the cross-sectional view depicted in FIG. 7) and the rear tip of a penile prosthesis cylinder or a RTE is inserted therein, lip 260 can exert force against and disfigure the rear tip or the RTE.

Figure 8:
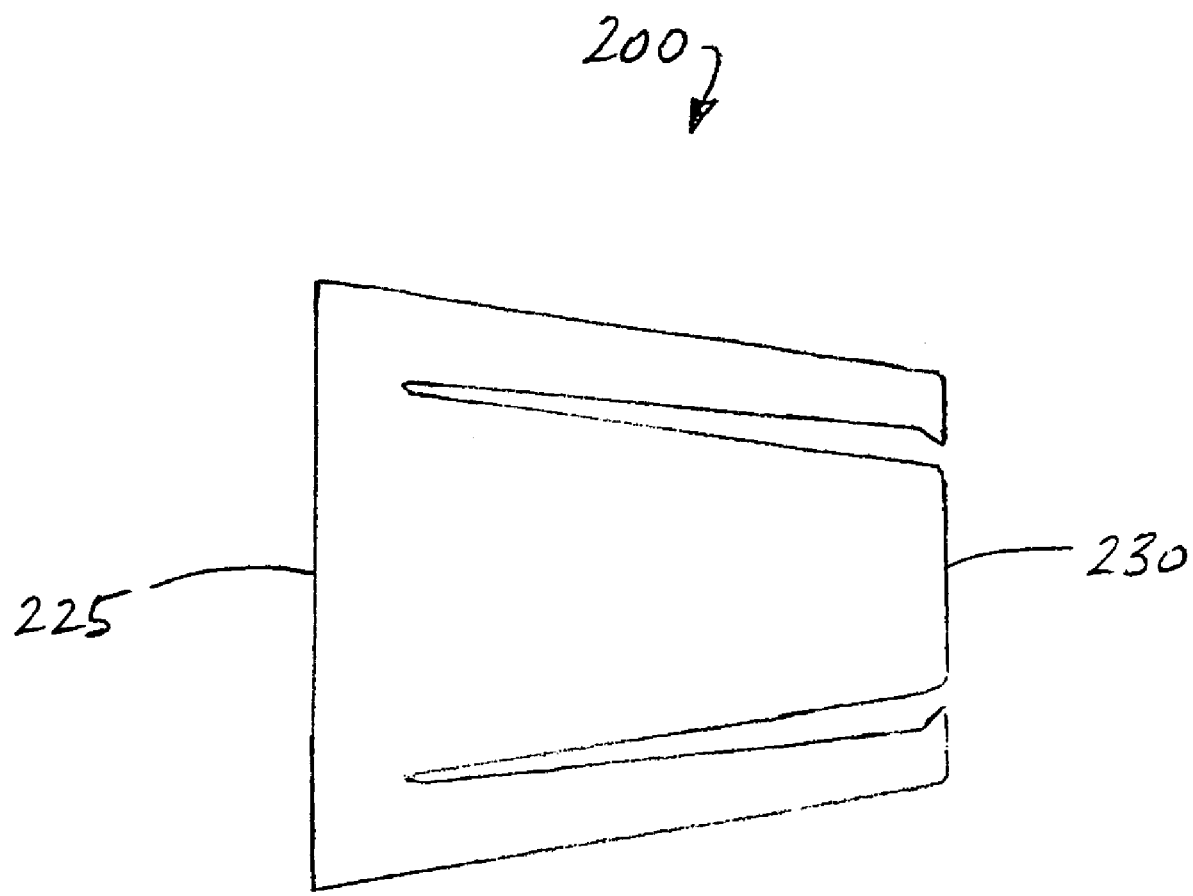
FIG. 8 is a side view of an adapter having bottom and top surfaces in parallel planes.
Figure 9:
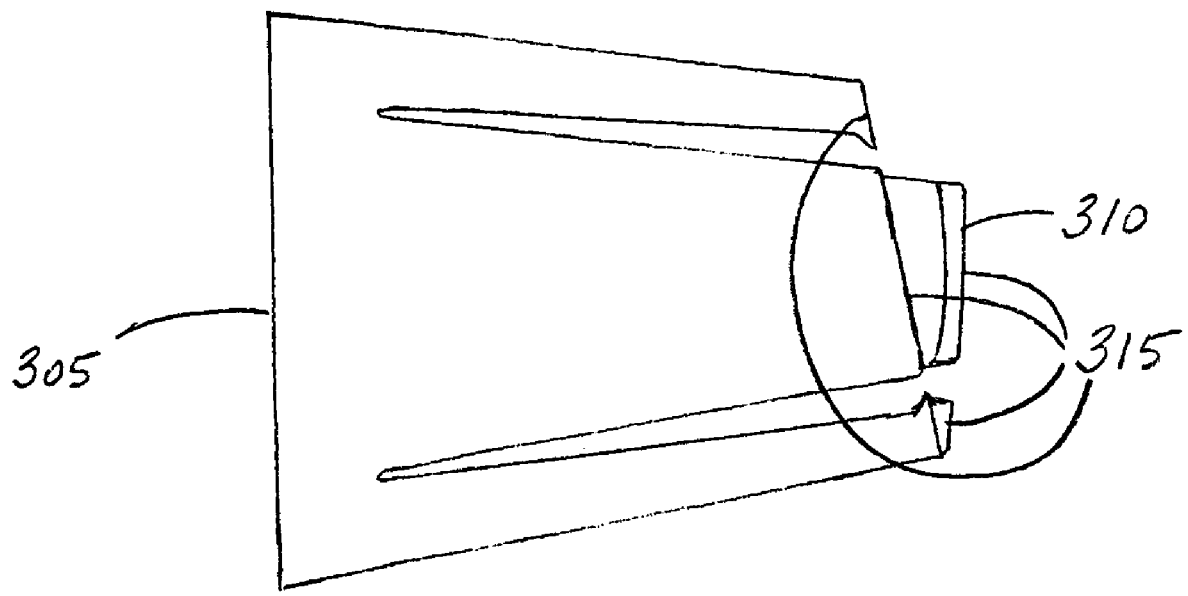
FIG. 9 is a side view of an adapter having a top surface that defines a threaded pitch.

With reference to FIGS. 8 and 9, an adapter such as adapter 100 or adapter 200 can be configured such that its bottom surface and its top surface lie in parallel planes or in non-parallel planes. For example, adapter 200 (FIG. 8) can have bottom surface 225 and top surface 230 that lie in parallel planes. A clinician (e.g., a surgeon or a surgical assistant) can assemble adapter 200 onto the rear tip of a penile prosthesis cylinder or onto the outer surface of a RTE using axial force. As shown in FIG. 8, top surface 230 of adapter 200 can lie in a single plane that is parallel to the plane in which bottom surface 225 lies. Alternatively, the different sections of top surface 225 can lie in two or more different planes that all are parallel to the plane in which bottom surface 225 lies.

Alternatively, adapter 300 (FIG. 9) can have bottom surface 305 and top surface 310 that are not in parallel planes. Top surface 310 of adapter 300 can lie in a single plane that is not parallel to the plane in which bottom surface 305 lies. Alternatively, the different sections of top surface 310 can lie in two or more different planes that are not parallel to the plane in which bottom surface 305 lies. As shown, for example, top surface 310 (and thus lip 315) can have a threaded pitch. A clinician can assemble adapter 300 onto the rear tip of a penile prosthesis cylinder or onto the outer surface of a RTE using rotational force only or using axial force combined with rotational force. For example, the rear tip of a cylinder or a RTE can be "screwed" into adapter 300. While adapter 300 can prevent accidental separation of the rear tip from an RTE, the threaded pitch of adapter 300 can facilitate removal of the rear tip from a RTE if, for example, a different size RTE is desired.

The adapters described herein can be installed on an outer surface of the rear tip of a penile prosthesis cylinder or on an outer surface of a RTE by a clinician (e.g., a surgeon or a surgical assistant) at or near the time of implantation. An adapter can be installed on a rear tip or on a first RTE prior to insertion of the rear tip or the first RTE into a second RTE. Alternatively, an adapter can be inserted into a RTE prior to insertion of a rear tip. In fact, an article of manufacture can include a RTE having an adapter pre-installed therein, such that a clinician only has to insert the rear tip of a cylinder into the RTE/adapter assembly. An adapter can be held within a RTE by a friction fit or mechanical interference. Alternatively, an adapter can be adhered to the interior surface of an RTE using, for example, an adhesive such as silicone, an acrylic, an epoxy, polyurethane, or cyanoacrylate.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A penile prosthesis comprising:
an inflatable, implantable cylinder configured for implantation into a corpus cavernosae and having a front end and a rear tip:
a rear tip extender having an opening for receiving the rear tip so as to effectively lengthen the implantable cylinder;
an adapter separable from and configured to engage the rear tip, the adapter including one or more protrusions configured to exert force against the rear tip and providing an outer surface to engage and retain the rear tip extender so as to effectively couple the rear tip extender to the rear tip.

2. The adapter of claim 1, wherein said adapter further comprises two or more discrete fingers configured to permit flexation towards an interior.

3. The adapter of claim 1, wherein said adapter comprises side surfaces that are parallel to one another.

4. The adapter of claim 1, wherein said adapter comprises side surfaces that are angled with respect to one another.

5. The adapter of claim 1, wherein said adapter has an outer diameter between about 5 mm and about 30 mm.

6. The adapter of claim 1, wherein said adapter has an outer diameter between about 10 mm and about 15 mm.

7. The adapter of claim 1, wherein said adapter comprises a bottom surface that lies within a plane, wherein each of said one or more protrusions comprises a top surface, and wherein each of said top surfaces lies within a plane that is parallel to the plane in which said bottom surface lies.

8. An article of manufacture comprising a rear tip extender for a penile prosthesis cylinder and the adapter of claim 1, wherein said rear tip extender is in the form of a hollow cone, and wherein said adapter is disposed within the interior of said rear tip extender.

9. The article of manufacture of claim 8, wherein said adapter is adhered to the interior surface of said rear tip extender.

10. The penile prosthesis of claim 1, wherein said one or more protrusions extend at an angle between about 5 degrees and about 140 degrees from the sides of said adapter.

11. An adapter for holding a rear tip extender onto an outer portion of the rear tip of a penile prosthesis cylinder or another rear tip extender, wherein said adapter fits over said outer portion and within said rear tip extender, wherein said adapter comprises one or more protrusions to exert force against said rear tip when said adapter is installed upon said outer portion, and wherein said one or more protrusions extend at an angle between about 5 degrees and about 140 degrees from the sides of said adapter, wherein said adapter comprises a bottom surface that lies within a plane, wherein each of said one or more lips comprises a top surface, and wherein each of said top surfaces lies within a plane that is not parallel to the plane in which said bottom surface lies.

12. The adapter of claim 11, wherein said top surfaces define a threaded pitch.

* * * * *

UNITED STATES PATENT AND TRADEMARK OFFICE
CERTIFICATE OF CORRECTION

PATENT NO.        : 7,648,456 B2                                    Page 1 of 1
APPLICATION NO. : 11/096478
DATED             : January 19, 2010
INVENTOR(S)       : Martin T. Steele, Sr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1312 days.

Signed and Sealed this

Twenty-eighth Day of December, 2010

David J. Kappos
*Director of the United States Patent and Trademark Office*